(12) United States Patent
Matsumoto et al.

(10) Patent No.: US 11,660,026 B2
(45) Date of Patent: May 30, 2023

(54) RESTORING A WEARABLE BIOLOGICAL SENSOR

(71) Applicant: International Business Machines Corporation, Armonk, NY (US)

(72) Inventors: Keiji Matsumoto, Yokohama (JP); Takahito Watanabe, Yokohama (JP); Eiji Nakamura, Kawasaki (JP); Patrick Ruch, Pratval (CH); Hiroyuki Mori, Yasu (JP)

(73) Assignee: International Business Machines Corporation, Armonk, NY (US)

(*) Notice: Subject to any disclaimer, the term of this patent is extended or adjusted under 35 U.S.C. 154(b) by 716 days.

(21) Appl. No.: 16/689,208

(22) Filed: Nov. 20, 2019

(65) Prior Publication Data
US 2021/0145325 A1    May 20, 2021

(51) Int. Cl.
*A61B 5/11*      (2006.01)
*A61B 5/00*      (2006.01)
(Continued)

(52) U.S. Cl.
CPC ........ *A61B 5/14517* (2013.01); *A61B 5/1127* (2013.01); *A61B 5/279* (2021.01);
(Continued)

(58) Field of Classification Search
CPC . A61B 5/14517; A61B 5/1127; A61B 5/6802; A61B 5/6815; A61B 5/681; A61B 5/01; A61B 5/6817; A61B 2562/24; A61B 5/263–268; A61B 5/276; A61B 5/279; A61B 5/282; A61B 2562/12; A61B 2562/125; A61B 2562/0209;
(Continued)

(56) References Cited

U.S. PATENT DOCUMENTS 4,543,958 A * 10/1985 Cartmell ................ A61B 5/259
                                                              600/397
8,128,801 B2    3/2012    Mansour et al.
(Continued)

FOREIGN PATENT DOCUMENTS

WO      2017058806 A1     4/2017

*Primary Examiner* — David J. McCrosky
*Assistant Examiner* — Nidhi N Patel
(74) *Attorney, Agent, or Firm* — Donald J. O'Brien

(57) ABSTRACT

Embodiments are disclosed for a method for restoring a wearable biological sensor. The method includes determining that a wearable biological marker sensor comprising a reference electrode is placed within a restoration apparatus. The restoration apparatus includes a correct reference electrode, a counter electrode, and a chloride solution. The reference electrode is in electrical contact with the correct reference electrode and the counter electrode through the chloride solution. The method additionally includes determining whether the reference electrode is degraded based on a voltage differential between the reference electrode and the correct reference electrode. The method also includes restoring the reference electrode, if the reference electrode is degraded, by applying a voltage to a circuit. The circuit includes the reference electrode and the counter electrode. Further, multiple chloride ions of the chloride solution bond with a plurality of silver atoms of the reference electrode.

20 Claims, 6 Drawing Sheets

(51) Int. Cl.
  *A61B 5/279* (2021.01)
  *A61B 5/265* (2021.01)
  *A61B 5/282* (2021.01)
  *A61B 5/145* (2006.01)
  *G01N 33/49* (2006.01)

(52) U.S. Cl.
  CPC ............ *A61B 5/681* (2013.01); *A61B 5/6817* (2013.01); *G01N 33/492* (2013.01); *A61B 5/265* (2021.01); *A61B 5/282* (2021.01); *A61B 2562/0215* (2017.08); *A61B 2562/125* (2013.01); *A61B 2562/24* (2013.01)

(58) Field of Classification Search
  CPC .... A61B 2562/0215; A61B 2562/0217; A61B 5/14507; A61B 5/14521; A61B 5/14539; A61B 5/14546; A61B 5/1468–14865; A61B 5/4266; G01N 33/492; G01N 27/4075–4077; G01N 27/4115–4118; G01N 27/38; G01N 27/301; G01N 27/3271; G01N 27/333
  See application file for complete search history.

(56) References Cited

U.S. PATENT DOCUMENTS

| | | |
|---|---|---|
| 2013/0273402 A1* | 10/2013 | Tsutsumi ................. C25D 9/06 429/188 |
| 2017/0023518 A1 | 1/2017 | Rowe et al. |
| 2017/0325724 A1 | 11/2017 | Wang et al. |
| 2018/0116514 A1* | 5/2018 | Turner .................... G16H 40/63 |
| 2018/0263539 A1* | 9/2018 | Javey .................... A61B 5/1477 |
| 2019/0268707 A1* | 8/2019 | Solum ...................... A61B 5/01 |
| 2020/0143085 A1* | 5/2020 | Cooner ............... G06F 21/6263 |

* cited by examiner

RESTORING A WEARABLE BIOLOGICAL SENSOR

BACKGROUND

The present disclosure relates to a charger, and more specifically, to an electrical charger.

There are three biological markers for heat-stroke that can be useful for the detection and prevention of heat stroke: core body temperature, sweat rate, and in-body sodium (Na+) concentration. Advantageously, these biological markers can be detected and/or determined at the epidermis. The sweat rate can be determined directly using a biological senor on the skin, or epidermis. However, the core body temperature and in-body Na+ concentrations may be determined indirectly by correlation with epidermal temperature and epidermal Na+ concentration, respectively.

SUMMARY

Embodiments are disclosed for a method for restoring a wearable biological sensor. The method includes determining that a wearable biological marker sensor comprising a reference electrode is placed within a restoration apparatus. The restoration apparatus includes a correct reference electrode, a counter electrode, and a chloride solution. The reference electrode is in electrical contact with the correct reference electrode and the counter electrode through the chloride solution. The method additionally includes determining whether the reference electrode is degraded based on a voltage differential between the reference electrode and the correct reference electrode. The method also includes restoring the reference electrode, if the reference electrode is degraded, by applying a voltage to a circuit. The circuit includes the reference electrode and the counter electrode. Further, multiple chloride ions of the chloride solution bond with a plurality of silver atoms of the reference electrode.

Further aspects of the present disclosure are directed toward systems and computer program products with functionality similar to the functionality discussed above regarding the computer-implemented methods. The present summary is not intended to illustrate each aspect of, every implementation of, and/or every embodiment of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
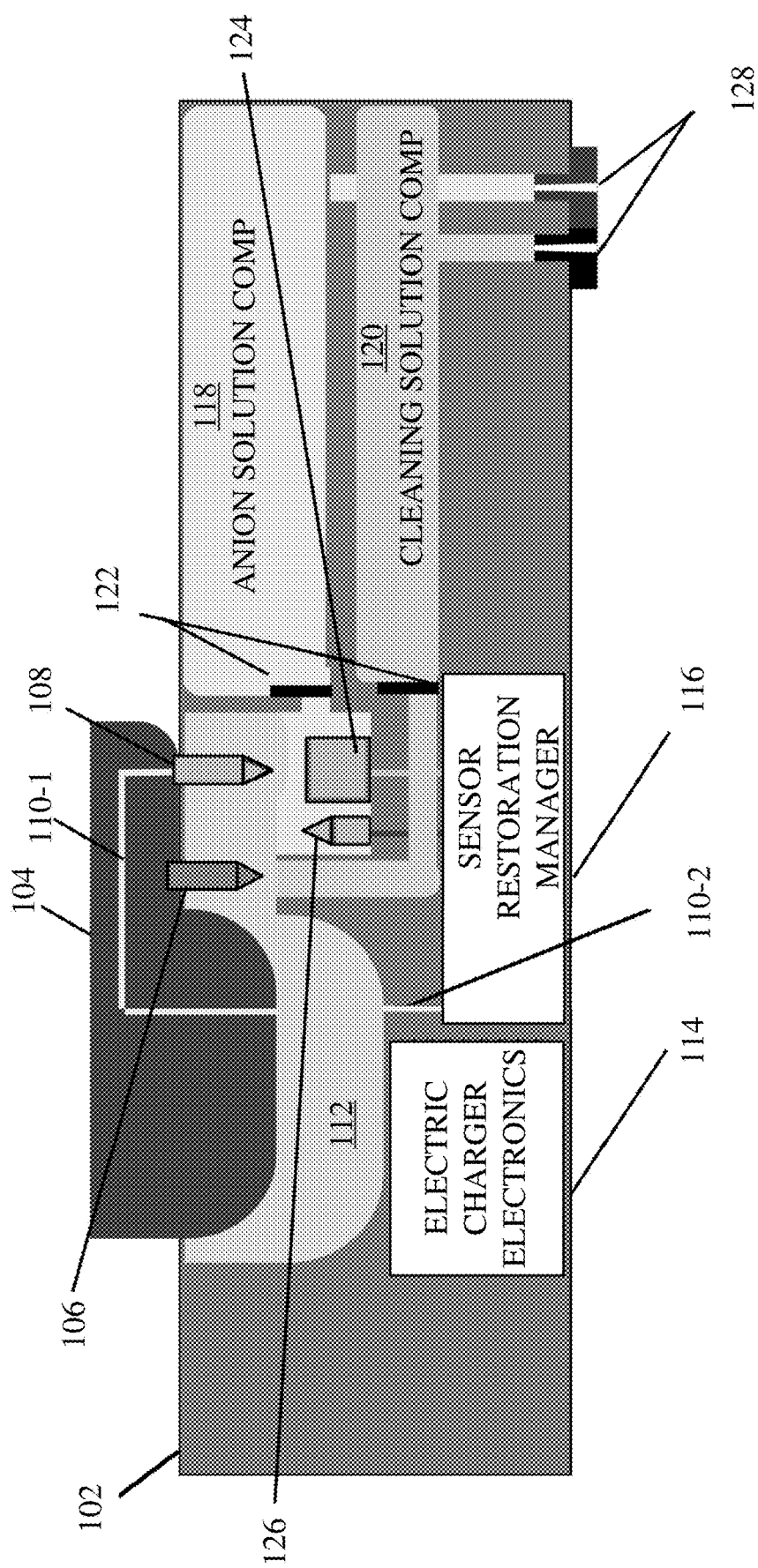
FIG. 1 is a block diagram of a restoration apparatus for a wearable biological marker sensor, in accordance with some embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

Advantageously, biological marker sensors such as described above can be incorporated into wearable items, such as watches, jewelry, earbud speakers, and the like. In this way, a sensor incorporated into the wearable item comes into contact with the skin consequentially. For example, the wearable biological marker sensor can be incorporated into the earbud of a hearing aid. In this way, the wearable biological marker sensor can monitor temperature, sweat rate, and Na+ concentration whenever the earbud is placed in the ear of the wearer. Advantageously, being able to monitor these biological markers can make it possible to alert the wearer if the measurements indicate a potential health issue.

In contrast to the sensors for temperature and sweat rate, sensors for Na+ concentration can chemically interact with the epidermal environment. This chemical interaction can degrade the sensor to the point that the sensor's measurements become unreliable. More specifically, a Na+ concentration sensor can include two electrodes: a sensing electrode and a reference electrode. The sensing electrode, when in contact with the skin, can measure the amount of sodium present in sweat, for example. In some Na+ sensing applications, no current flows between the sensing and reference electrode. Rather, a voltage is measured under open-circuit conditions. However, the reference electrode can be composed of silver (Ag) and a silver salt, such as silver chloride (AgCl). Due to the solubility of AgCl, chloride ions may dissolve in the liquid sweat, leaving the silver atoms behind on the reference electrode. The depletion of chloride from an Ag/AgCl reference electrode can cause its potential to vary, which leads to an unreliable determination of the Na+ concentration. However, replacing the electrodes in such sensors can be a challenge because the sensors are relatively small, and thus, can be challenging to handle. Further, such replacement may be costly, and dangerous.

It is possible to re-bond chloride ions with the silver atoms of a degraded sensor, therein replenishing the silver chloride molecules on the reference electrode. However, in some chemical reactions, flammable gas may be produced. For example, placing the degraded silver reference electrode in a solution of hydrogen chloride can re-combine chlorine and silver atoms on the reference electrode, but also produce flammable hydrogen ($H_2$) gas. Thus, if the $H_2$ gas were to exceed the explosion limit of the ambient air, the gas could ignite if the sensor were to conduct its electrical circuit, unintentionally or otherwise.

Another potential source of ignition for such gas can be batteries that can be incorporated into wearable electronic sensors as described above. The battery provides the advantage of mobility for the device, however, it also means the battery is recharged periodically. The period of time for replenishing a battery can also provide an opportunity to replenish degraded reference electrodes on the wearable electronic device.

Accordingly, some embodiments of the present disclosure can provide an electrical charger for a wearable electronic device having a biological marker sensor. In addition to replenishing a battery, the electrical charger can replenish degraded reference electrodes of the wearable biological marker sensor. The electrical charger can replenish the degraded reference electrodes while the battery recharges, using a chemical reaction that produces an inflammable chemical by-product. In this way, some embodiments of the present disclosure provide an apparatus that safely restores the chemical and electrical properties of wearable biological marker sensors.

FIG. 1 is a block diagram of a restoration apparatus 102 for a wearable biological marker sensor 104, in accordance with some embodiments of the present disclosure. The wearable biological marker sensor 104 can be an earbud, for example. The earbud can include a measurement sensor 106, reference electrode 108, an electrical connector 110-1. The measurement sensor 106 may conduct an electrical current in a circuit with the reference electrode 108 to measure the Na+ concentration of the epidermis of the wearer of the earbud. In some embodiments of the present disclosure, the reference electrode 108 can include a silver element and a silver-coating, such as, copper (Cu) tungsten (W), silver chloride (AgCl), silver bromide (AgBr), silver iodide (AgI), and silver sulfide ($Ag_2S$). The reference electrode 108 can alternatively include a mercury element and a mercury coating, such as mercury chloride ($Hg_2Cl_2$). These are merely examples, and do not include an exhaustive list of potential materials for the reference electrode 108. In order to recharge a battery (not shown) of the wearable biological marker sensor 104, the wearable biological marker sensor 104 can be placed in a cavity 112 of the restoration apparatus 102. The cavity 112 can be an opening of the restoration apparatus 102 that is configured to accommodate the shape of the wearable biological marker sensor 104. In this case, the cavity 112 accommodates the shape of the earbud. When placed within the cavity 112, the wearable biological marker sensor 104 can come into electrical contact with electric charger electronics 114 of the restoration apparatus 102, which can include electronic circuitry providing electrical power that re-charges the battery of the wearable biological marker sensor 104.

Additionally, when placed within the cavity 112, the electrical connector 110-1 (of the earbud) can come into electrical contact with the electrical connector 110-2 (of the restoration apparatus 102). The electrical connectors 110-1 and 110-2 can thus create an electrical connection between the reference electrode 108 and sensor restoration manager 116. The sensor restoration manager 116 can include electronic circuitry that provides electrical power used to replenish degradation of the reference electrode 108.

More specifically, the restoration apparatus 102 may additionally include an anion solution compartment (COMP) 118 and a cleaning solution compartment 120. The anion solution compartment 118 can contain an anion solution. The anion in the solution can form a compound with a material portion, e.g., the coating, of the reference electrode 108 with restoration. The anion solution can include bromide, iodide, and chloride solutions, which may vary depending on the coating of the reference electrode 108. For example, chloride solutions can be used for silver chloride coated reference electrodes 108. Some chloride solutions include hydrogen chloride (HCl), sodium chloride (NaCl), or potassium chloride (KCl), for example. Thus, a chloride solution can be used to replenish the silver chloride on the reference electrode 108 when the wearable biological marker sensor 104 is placed within the cavity 112. In some cases, the chloride solution may be acidic. As such, the anion solution compartment 118 and the cavity 112 can be acid resistant. Accordingly, the anion solution compartment 118 and the cavity 112 can be made of, for example, poly-vinyl chloride (PVC), acrylonitrile butadiene styrene (ABS), polyethylene, polypropylene, polytetrafluoroethylene (PTFE), or epoxy.

The reaction of the chloride in the chloride solution with silver on the reference electrode 108 produces silver chloride, which can be used to restore the reference electrode 108. Additionally, with a sodium chloride solution, as the sodium is dissolved as ions, it does not participate in any reactions. The electrochemical reactions taking place with a sodium chloride solution are represented in EXAMPLE REACTION 1:

REFERENCE ELECTRODE: Ag(s)+Cl−(aq)=> AgCl(s)+e−

COUNTER ELECTRODE: At high pH: 2H+(aq)+ 2e−=>$H_2$(g)

At low pH: $2H_2O$(l)+2e−=>$H_2$(g)+ 2OH−(aq)          EXAMPLE REACTION 1

Additionally, the restoration manager 116 can safely manage the $H_2$ gas produced by the EXAMPLE REACTION 1. This technique is described in greater detail below.

Additionally, the anion solution compartment 118 and cleaning solution compartment 120 can include valves 122 for openings into the cavity 112. Thus, when the earbud is placed within the cavity 112, the valves 122 can open in response to corresponding pressure, allowing the chloride and cleaning solutions to pass into openings in the cavity 112 for the reference electrode 108 and measurement sensor 106, respectively. In this way, the measurement sensor 106 can come into contact with the cleaning solution, which may dissolve physical and chemical bonds between the dirt, grime, oils, etc., and the surface of the measurement sensor 106.

According to some embodiments of the present disclosure, the restoration apparatus 102 can include a latch (not shown) that is manually activated by placing the wearable biological marker sensor 104 into the restoration apparatus 102. Alternatively, the restoration apparatus 102 can include a button (not shown) that can be manually pressed once the wearable biological marker sensor 104 is placed into the restoration apparatus 102. Thus, once the latch is activated or the button pressed, the restoration apparatus 102 can open the valves 122 and begin the restoration. In some embodiments of the present disclosure, the restoration apparatus 102 can include a capacitive proximity sensor or magnetic reed switch, which could also detect the presence of the wearable biological marker sensor 104. Alternatively, the sensor restoration manager 116 can monitor the electrical resistance between the electrical connector 110-1 and electrical connector 110-2. Upon insertion of the wearable biological marker sensor 104, there can be a sudden and pronounced drop in resistance.

Similarly, placing the wearable biological marker sensor 104 into the cavity 112 brings the reference electrode 108 into contact with the chloride solution. Additionally, this placement brings the reference electrode 108 into ionic contact with a counter electrode 124, which can be in electrical contact with the sensor restoration manager 116. Thus, providing power from the sensor restoration manager 116 to the circuit including the reference electrode 108 and the counter electrode 124 can complete an electrical circuit. Completing this electrical circuit initiates an electro-chemical reaction wherein the chloride ions from the chloride solution can chemically bond with the silver atoms of the reference electrode 108. In this way, the chemical and electrical properties of the degraded reference electrode 108 can be restored. In some embodiments of the present disclosure, the counter electrode 124 can be composed of copper, palladium, gold, carbon, tin, zinc, and silver.

Further, the opening in the cavity 112 for the reference electrode 108 can include a correct reference electrode 126. The correct reference electrode 126 contains the same material combination as the reference electrode 108. For example, if the reference electrode 108 is composed of silver and silver chloride, the correct reference electrode 126 can be composed of silver and silver chloride. Further, the correct reference electrode 126 can be in electrical contact with the sensor restoration manager 116. Thus, providing power from the sensor restoration manager 116 to the circuit including the reference electrode 108, the chloride solution, and the correct reference electrode 126 can initiate an electro-chemical reaction wherein the amount of silver chloride on the reference electrode 108 can be measured. More specifically, the voltage difference between the reference electrode 108 and the correct reference electrode 126 is measured. If there is no voltage difference, the chemical restoration of the reference electrode 108 may be complete. In this way, the correct reference electrode 126 provides a reference for how much silver chloride to restore to the reference electrode 108.

Accordingly, the sensor restoration manager 116 can include circuitry that provides power to the counter electrode 124 and the correct reference electrode 126 to restore and measure the silver chloride on the reference electrode 108. Accordingly, the restoration apparatus 102 can measure the amount of silver chloride on the reference electrode 108, determine whether the reference electrode 108 is degraded, and if so, provide power to the counter electrode 124 in order to bind chloride ions to the silver atoms of the reference electrode 108. In this way, the restoration apparatus 102 can automatically detect a degraded reference electrode 108 and apply power and chloride solution until the silver chloride on the reference electrode 108 is restored to the level of the correct reference electrode 126.

In addition, the restoration manager 116 can monitor the amount of by-product, e.g., $H_2$ gas, produced during the restoration of the reference electrode 108. More specifically, when the electrochemical reduction of water at the counter electrode 126 is used to balance the electrochemical oxidation of silver at the reference electrode 108, hydrogen gas may be produced at the surface of the counter electrode 126. Accordingly, the restoration manager 116 can monitor the current flowing during restoration of the reference electrode 108, and provide an estimate of the amount of hydrogen gas produced according to Faraday's law. Faraday's law can be expressed as, $n=It/(2F)$, where n is the number of molecules of hydrogen, I is the current, t is the duration of current flow, and F is Faraday's constant. Thus, the restoration manager 116 can limit the rate of production of hydrogen gas to avoid reaching the flammability limit, e.g. by limiting the concentration of hydrogen produced to less than 4% by volume. Further, the chloride solution can include an oxidizing agent instead of water. In this way, the chloride solution can prevent the accumulation of hydrogen at the counter electrode 126. In some embodiments, the oxidizing agent can be potassium hexacyanoferrate (III).

Over time, the chloride and cleaning solutions can be depleted by such use of the restoration apparatus 102. Accordingly, the restoration apparatus 102 can include refill ports 128 with openings to the anion solution compartment 118 and cleaning solution compartment 120, through which chloride and cleaning solutions can be re-filled.

Figure 2:
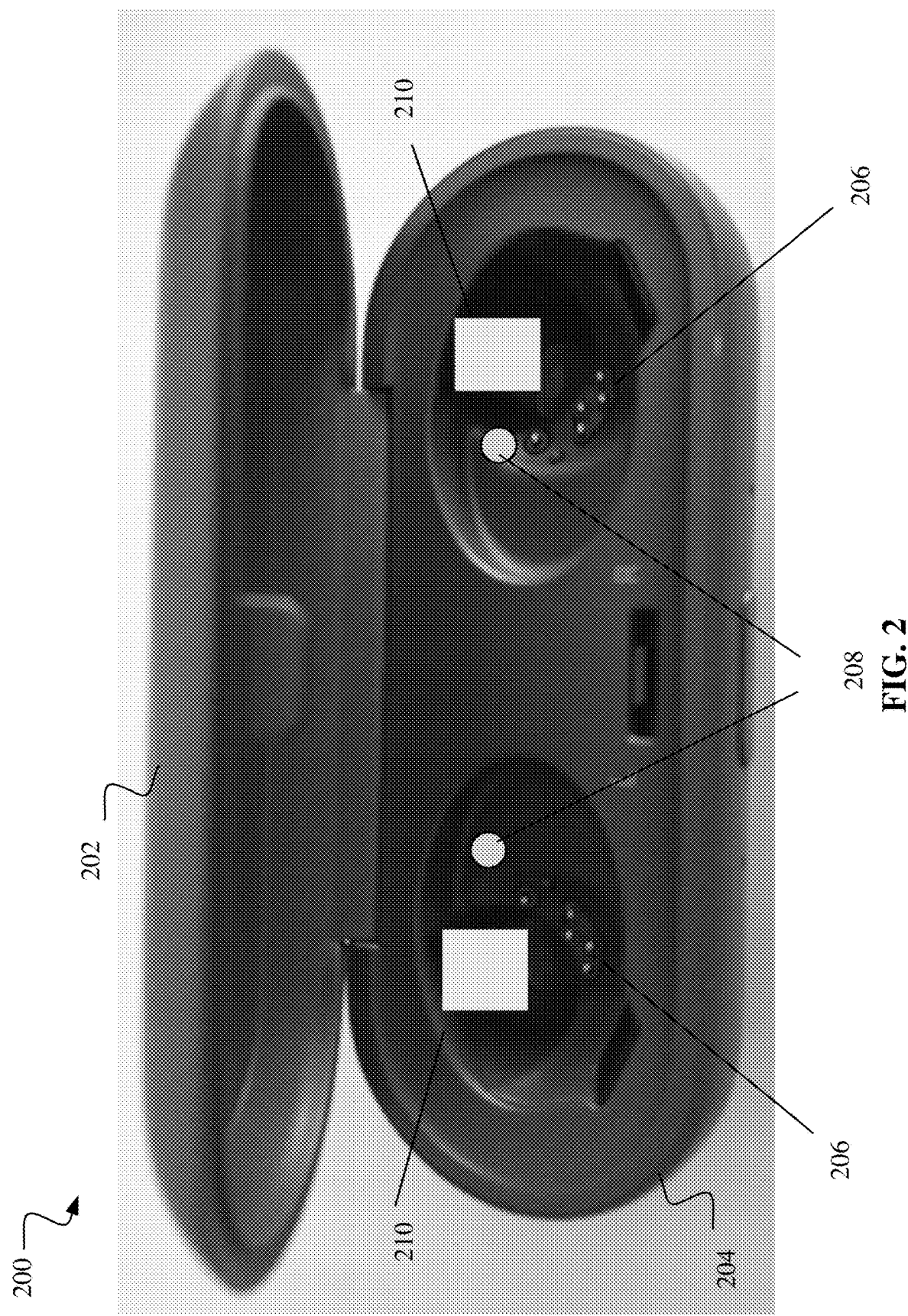
FIG. 2 is a block diagram of an example restoration apparatus, in accordance with some embodiments of the present disclosure.

FIG. 2 is a block diagram of an example restoration apparatus 200, in accordance with some embodiments of the present disclosure. The restoration apparatus 200 can be configured in the shape of a case, such as a case to hold eyeglasses, earbuds, and the like. In this example, the restoration apparatus includes a lid 202 and a base 204. The lid 202 may be hinged to the base 204 to make it possible to enclose earbuds securely within the case. The base 204 can include left "L" and right "R" cavities for each earbud. The cavities can each include electrical contacts 206 for recharging a battery of a wearable biological sensor incorporated into the earbud, such as the wearable biological marker sensor 104 described with respect to FIG. 1. Additionally, the cavities include sensor electrode openings 208. The sensor electrode openings 208 can provide a receptacle for the sensor electrode of the wearable biological marker sensor 104 when placing the earbuds in the restoration apparatus 200. Additionally, the sensor electrode openings 208 can include cleaning solution that may clean sensor electrodes, such as the measurement sensor 106.

The base 204 of the restoration apparatus 200 can also include reference electrode openings 210. The reference electrode openings 210 can provide a receptacle for the reference electrodes, such as the reference electrode 108. Further the reference electrode openings 210 can contain a chloride solution, such as sodium chloride, which can be used to restore silver chloride to the reference electrodes 108. The reference electrode openings 210 can also include a correct reference electrode (not shown) and counter electrode (not shown), such as the correct reference electrode 126 and counter electrode 124 described with respect to FIG. 1. Thus, the restoration apparatus 200 can be configured to restore the electrical and chemical properties of earbuds that incorporate wearable biological marker sensors 104.

Figure 3A:
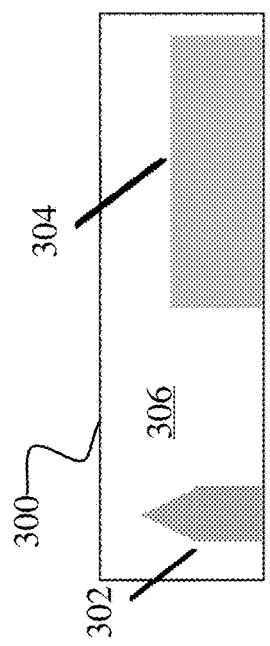
FIG. 3A is a side view of an example reference electrode opening of a restoration apparatus, in accordance with some embodiments of the present disclosure.

FIG. 3A is a side view of an example reference electrode opening 300 of a restoration apparatus, in accordance with some embodiments of the present disclosure. The reference electrode opening 300 includes a correct reference electrode 302, a counter electrode 304, and a chloride solution 306. The correct reference electrode 302 may be similar to the correct reference electrode 126 described with respect to FIG. 1. Additionally, the counter electrode 302 can be similar to the counter electrode 124 described with respect to FIG. 1. The chloride solution 306 can be similar to the chloride solution in the anion solution compartment 118 described with respect to FIG. 1. In some embodiments, the chloride solution can be a sodium chloride solution dissolved in water.

Figure 3B:
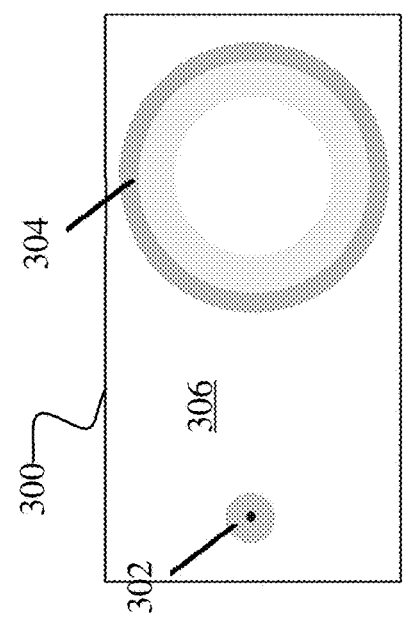
FIG. 3B is a top view of an example reference electrode opening of a restoration apparatus, in accordance with some embodiments of the present disclosure.

FIG. 3B is a top view of an example reference electrode opening 300 of a restoration apparatus, in accordance with some embodiments of the present disclosure. The reference electrode opening 300 includes the correct reference electrode 302, counter electrode 304, and chloride solution 306. Further, by using the example reference electrode opening 300, a uniform thickness of AgCl can be restored on the reference electrode 108 because the counter electrode 304 is a circular shape and when current is applied, the electrical field may be uniform between the reference electrode 108 and the counter electrode 304.

Figure 3C:
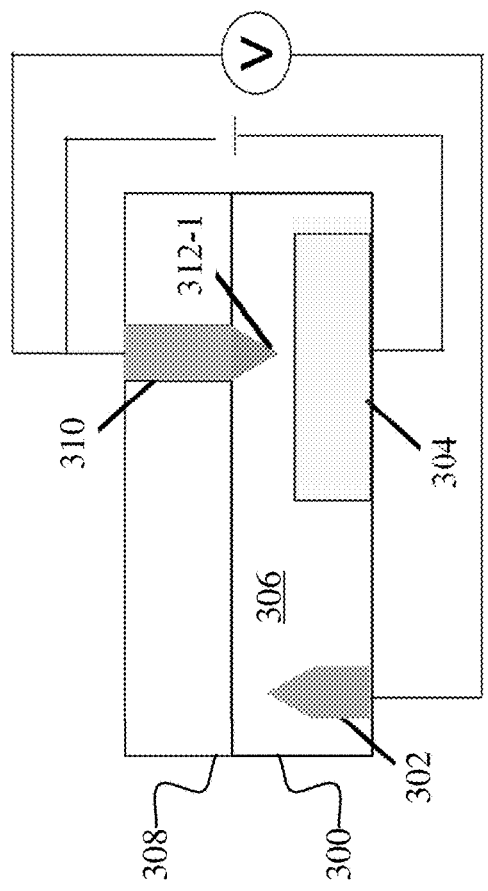
FIG. 3C is a side view of an example reference electrode opening of a restoration apparatus in contact with an example wearable biological marker sensor with current applied, in accordance with some embodiments of the present disclosure.

FIG. 3C is a side view of an example reference electrode opening 300 of a restoration apparatus in contact with an example wearable biological marker sensor 308 with current applied, in accordance with some embodiments of the present disclosure. The wearable biological marker sensor 308 can be similar to the wearable biological marker sensor 104 described with respect to FIG. 1. Further, the wearable biological marker sensor 308 can include a reference electrode 310 with a degraded tip 312-1. In some embodiments of the present disclosure, the degraded tip 312-1 can be an exposed portion of the reference electrode 310 with silver left behind after the initial silver chloride compound has degraded from the chloride ions breaking their chemical bonds with the silver atoms of the degraded tip 312-1. The reference electrode 310 can be similar to the reference electrode 108 described with respect to FIG. 1.

Figure 3D:
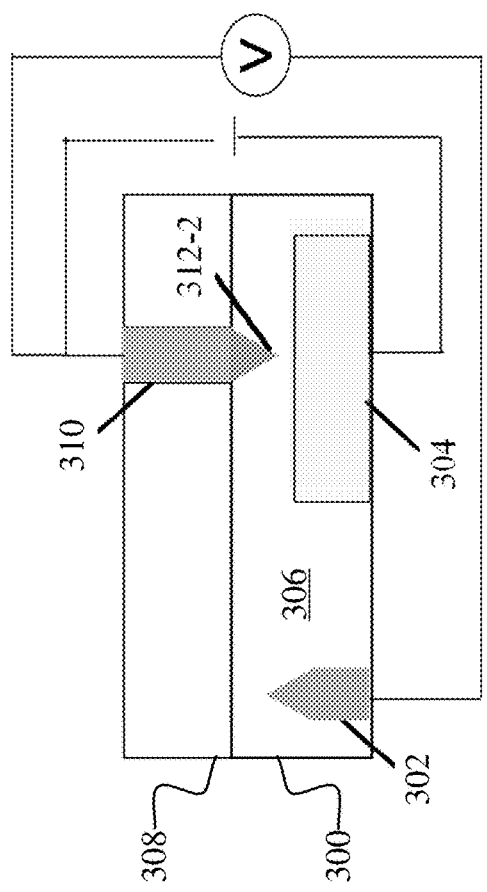
FIG. 3D is a side view of an example reference electrode opening of a restoration apparatus in contact with an example wearable biological marker sensor with current applied, in accordance with some embodiments of the present disclosure.

FIG. 3D is a side view of an example reference electrode opening 300 of a restoration apparatus in contact with an example wearable biological marker sensor 308 with current applied, in accordance with some embodiments of the present disclosure. As stated previously, by applying current to the electrical circuit including the reference electrode 310 and the counter electrode 304 in the chloride solution 306, chloride ions from the chloride solution 306 can bond with silver atoms of the reference electrode 310. Thus, the restored tip 312-2 can include the resultant silver chloride molecules from these chemical bonds.

Figure 4:
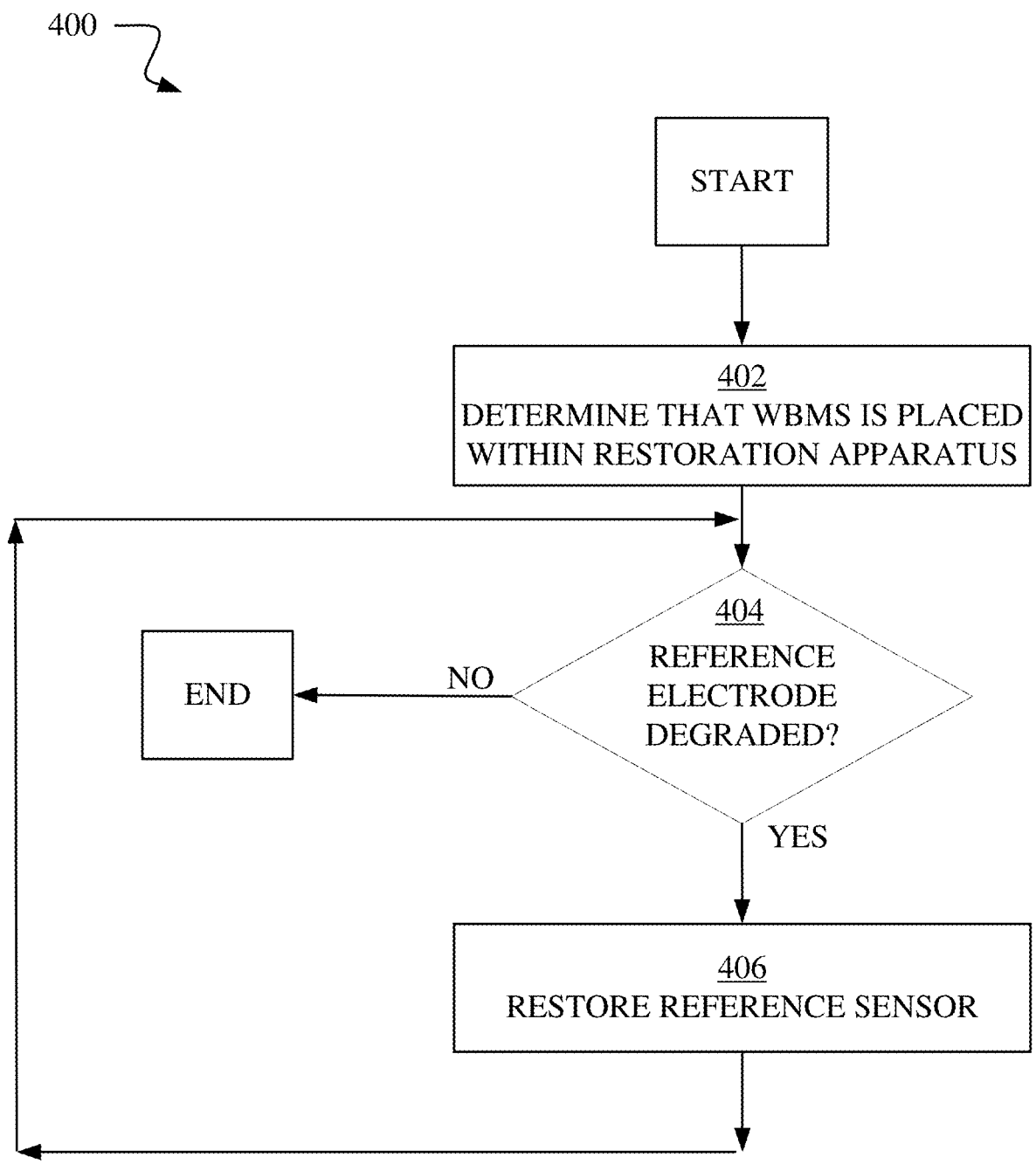
FIG. 4 is a process flow diagram of a method for restoring a wearable biological sensor, in accordance with some embodiments of the present disclosure.

FIG. 4 is a process flow diagram of a method 400 for restoring a wearable biological sensor, in accordance with some embodiments of the present disclosure. The method 400 can be performed by restoration electronics of a restoration apparatus, such as the sensor restoration manager 116 of the restoration apparatus 102 described with respect to FIG. 1.

At operation 402, the sensor restoration manager 116 can determine that a wearable biological marker sensor (WBMS), such as the wearable biological marker sensor 104 is placed within the restoration apparatus 102. Determining that the wearable biological marker sensor 104 is placed within the restoration apparatus 102 can involve determining that an electrical circuit is complete and including a reference electrode of the wearable biological marker sensor 104 and a counter electrode, such as the counter electrode 124 described with respect to FIG. 1. Alternatively, in some embodiments of the present disclosure, determining that the wearable biological marker sensor 104 is placed within the restoration apparatus 102 can involve manually activating a latch of the restoration apparatus 102 by placing the wearable biological marker sensor 104 into the restoration apparatus 102. As stated previously, in some embodiments of the present disclosure, the restoration apparatus 102 can include a button (not shown) that can be manually pressed once the wearable biological marker sensor 104 is placed into the restoration apparatus. In such embodiments, the sensor restoration manager 116 can determine that the wearable biological marker sensor 104 is placed within the restoration apparatus 102 when the button is pressed.

At operation 404, the sensor restoration manager 116 can determine if the reference electrode 108 is degraded. Determining if the reference electrode 108 is degraded can involve applying a current to the circuit including the correct reference electrode of the restoration apparatus 102 and the reference electrode 108. Any difference in voltage between the correct reference electrode 126 and the reference electrode 108 that is outside a predetermined threshold can represent a difference in the amount of silver chloride on the correct reference electrode 126 and the reference electrode 108. Thus, if the difference in the amount of voltage between the correct reference electrode 126 and the reference electrode 108 is outside of a predetermined constant value, the reference electrode 108 may be degraded. Accordingly, control can flow to operation 406. However, if the reference electrode 108 is not degraded, the method 400 can terminate.

At operation 406, the sensor restoration manager 116 can restore the reference electrode 108. For example, the sensor restoration manager 116 can apply electrical current to the circuit including the reference electrode 108 and the counter electrode 124. Applying electrical current in this way can cause an electro-chemical reaction that bonds the chloride ions in the chloride solution to the silver atoms of the reference electrode 108. This process is also referred to herein as chlorination. Additionally, control may flow to operation 404, where operations 404 and 406 can be repeated until the reference electrode has been restored Alternatively, an additional, temporary termination can be implemented to avoid dangerous accumulation of hydrogen gas. Since hydrogen diffuses easily, the hydrogen gas produced from an HCl solution can escape from the restoration apparatus 102 in a relatively short period of time. Therefore, following temporary termination of the restoration to avoid hydrogen accumulation, the restoration may resume after a few seconds to minutes by which time the hydrogen has cleared from the restoration apparatus. This temporary termination can include the sensor restoration manager 116 pausing the application of an electric charge for restoring the reference electrode 108.

Figure 5:
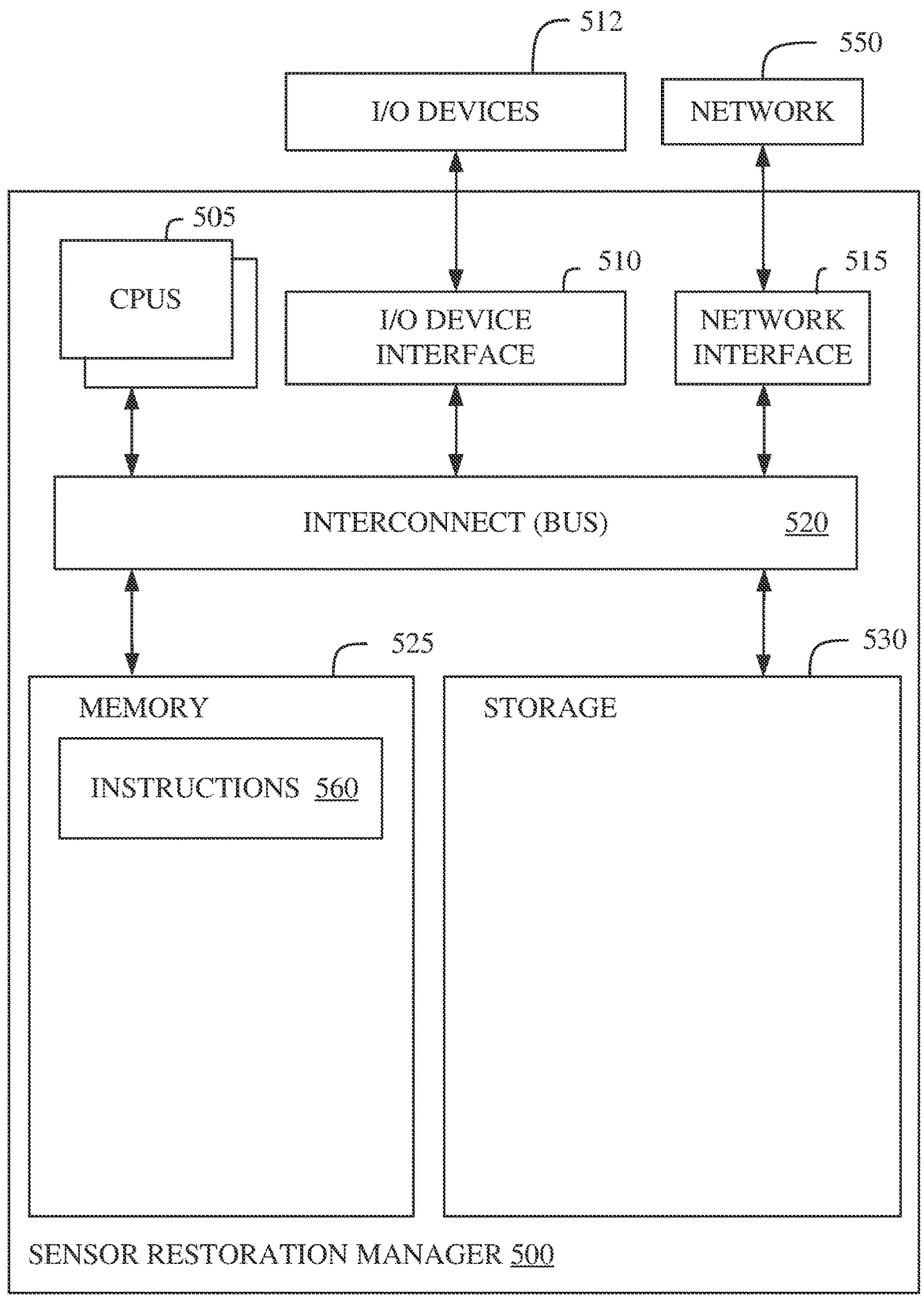
FIG. 5 is a block diagram of an example sensor restoration manager, in accordance with some embodiments of the present disclosure.

FIG. 5 is a block diagram of an example sensor restoration manager 500, in accordance with some embodiments of the present disclosure. In various embodiments, the sensor restoration manager 500 is similar to the sensor restoration manager 116 and can perform the method described in FIG. 4, and/or the functionality discussed in FIGS. 1, 2, and 3A-3D. In some embodiments, the sensor restoration manager 500 provides instructions for the aforementioned methods and/or functionalities to a client machine such that the client machine executes the method, or a portion of the method, based on the instructions provided by the sensor restoration manager 500. In some embodiments, the sensor restoration manager 500 comprises software executing on hardware incorporated into a plurality of devices.

The sensor restoration manager 500 includes a memory 525, storage 530, an interconnect (e.g., BUS) 520, one or more CPUs 505 (also referred to as processors 505 herein), an I/O device interface 510, I/O devices 512, and a network interface 515.

Each CPU 505 retrieves and executes programming instructions stored in the memory 525 or the storage 530. The interconnect 520 is used to move data, such as programming instructions, between the CPUs 505, I/O device interface 510, storage 530, network interface 515, and memory 525. The interconnect 520 can be implemented using one or more busses. The CPUs 505 can be a single CPU, multiple CPUs, or a single CPU having multiple processing cores in various embodiments. In some embodiments, a CPU 505 can be a digital signal processor (DSP). In some embodiments, CPU 505 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 525 is generally included to be representative of a random access memory (e.g., static random access memory (SRAM), dynamic random access memory (DRAM), or Flash). The storage 530 is generally included to be representative of a non-volatile memory, such as a hard disk drive, solid state device (SSD), removable memory cards, optical storage, and/or flash memory devices. Additionally, the storage 530 can include storage area-network (SAN) devices, the cloud, or other devices connected to the sensor restoration manager 500 via the I/O device interface 510 or to a network 550 via the network interface 515.

In some embodiments, the memory 525 stores instructions 560. However, in various embodiments, the instructions 560 are stored partially in memory 525 and partially in storage 530, or they are stored entirely in memory 525 or entirely in storage 530, or they are accessed over a network 550 via the network interface 515.

Instructions 560 can be processor-executable instructions for performing any portion of, or all, any of the method described in FIG. 4, and/or the functionality discussed in FIGS. 1, 2, and 3A-3D.

In various embodiments, the I/O devices 512 include an interface capable of presenting information and receiving input. For example, I/O devices 512 can present information to a listener interacting with sensor restoration manager 500 and receive input from the listener.

The sensor restoration manager 500 is connected to the network 550 via the network interface 515. Network 550 can comprise a physical, wireless, cellular, or different network.

In some embodiments, the sensor restoration manager 500 can be a multi-user mainframe computer system, a single-user system, or a server computer or similar device that has little or no direct user interface but receives requests from other computer systems (clients). Further, in some embodiments, the sensor restoration manager 500 can be implemented as a desktop computer, portable computer, laptop or notebook computer, tablet computer, pocket computer, telephone, smart phone, network switches or routers, or any other appropriate type of electronic device.

It is noted that FIG. 5 is intended to depict the representative major components of an exemplary sensor restoration manager 500. In some embodiments, however, individual components can have greater or lesser complexity than as represented in FIG. 5, components other than or in addition to those shown in FIG. 5 can be present, and the number, type, and configuration of such components can vary.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method, comprising:
   determining that a wearable biological marker sensor comprising a reference electrode is placed within a restoration apparatus that restores a coating of the reference electrode comprising:
   a correct reference electrode;
   a counter electrode; and
   an anion solution, wherein the reference electrode is in electrical contact with the correct reference electrode and the counter electrode through the anion solution;
   determining whether the reference electrode is degraded based on a voltage differential between the reference electrode and the correct reference electrode; and
   restoring the reference electrode, in response to determining that the reference electrode is degraded, by applying a voltage to a circuit comprising the reference electrode and the counter electrode wherein a plurality of bonding ions of an anion solution bond with a plurality of coating atoms of the reference electrode.

2. The method of claim 1, wherein the reference electrode is degraded when the voltage differential exceeds a predetermined constant value.

3. The method of claim 1, wherein the counter electrode comprises a chemical selected from a group consisting of copper, platinum, gold, carbon, palladium, tin, zinc, and silver.

4. The method of claim 1, wherein the counter electrode comprises a circular shape.

5. The method of claim 4, wherein the anion solution comprises a chloride solution comprising chloride ions, wherein the bonding ions are the chloride ions, and wherein the plurality of coating atoms comprises silver atoms.

6. The method of claim 5, wherein the circular shape causes a uniform thickness of silver chloride to form on the reference electrode.

7. The method of claim 5, wherein the restored reference electrode comprises silver chloride molecules.

8. The method of claim 1, wherein:
   the wearable biological marker sensor comprises a measurement electrode; and
   the restoration apparatus comprises a cleaning solution placed into contact with the measurement electrode by placing the wearable biological marker sensor in the restoration apparatus.

9. The method of claim 1, further comprising recharging a battery of the wearable biological marker sensor while the wearable biological marker sensor is placed within the restoration apparatus.

10. The method of claim 1, further comprising pausing restoring the reference electrode, in response to determining that a hydrogen gas is accumulating, wherein pausing allows the hydrogen gas to dissipate.

11. A computer program product comprising program instructions stored on a computer readable storage medium, the program instructions executable by a processor to cause the processor to perform a method comprising:
   determining that a wearable biological marker sensor comprising a reference electrode is placed within a restoration apparatus that restores a coating of the reference electrode comprising:
   a correct reference electrode;
   a counter electrode; and
   an anion solution, wherein the reference electrode is in electrical contact with the correct reference electrode and the counter electrode through the anion solution;
   determining whether the reference electrode is degraded based on a voltage differential between the reference electrode and the correct reference electrode, wherein the reference electrode is degraded if the voltage differential exceeds a predetermined constant value; and
   restoring the reference electrode, in response to determining that the reference electrode is degraded, by applying a voltage to a circuit comprising the reference electrode and the counter electrode wherein a plurality of bonding ions of an anion solution bond with a plurality of coating atoms of the reference electrode.

12. The computer program product of claim 11, wherein the counter electrode comprises a chemical selected from a group consisting of copper, palladium, gold, carbon, tin, zinc, and silver.

13. The computer program product of claim 11, wherein the counter electrode comprises a circular shape.

14. The computer program product of claim 13, wherein the anion solution comprises a chloride solution comprising chloride ions, wherein the bonding ions are the chloride ions, and wherein the plurality of coating atoms comprises silver atoms.

15. The computer program product of claim 14, wherein:
the circular shape causes a uniform thickness of silver chloride to form on the reference electrode; and
the restored reference electrode comprises silver chloride molecules.

16. The computer program product of claim 11, wherein:
the wearable biological marker sensor comprises a measurement electrode; and
the restoration apparatus comprises a cleaning solution placed into contact with the measurement electrode by placing the wearable biological marker sensor in the restoration apparatus.

17. The computer program product of claim 11, further comprising pausing restoring the reference electrode, in response to determining that a hydrogen gas is accumulating, wherein pausing allows the hydrogen gas to dissipate.

18. A system comprising:
a correct reference electrode;
a counter electrode comprising a circular shape;
a chloride solution compartment;
a computer processing circuit; and
a computer-readable storage medium storing instructions, which, when executed by the computer processing circuit, are configured to cause the computer processing circuit to perform a method comprising:
determining that a wearable biological marker sensor comprising a reference electrode is placed within the system, wherein the system restores a coating of the reference electrode;
determining whether the reference electrode is degraded based on a voltage differential between the reference electrode and the correct reference electrode, wherein the reference electrode is degraded when the voltage differential exceeds a predetermined constant value; and
restoring the reference electrode, if the reference electrode is degraded, by applying a voltage to a circuit comprising the reference electrode and the counter electrode wherein a plurality of chloride ions of a chloride solution from a chloride solution compartment bond with a plurality of silver atoms of the reference electrode.

19. The system of claim 18, comprising a cleaning solution compartment, wherein:
the wearable biological marker sensor comprises a measurement electrode; and
the cleaning solution compartment comprises a cleaning solution placed into contact with the measurement electrode by placing the wearable biological marker sensor in the system.

20. The system of claim 18, the method further comprising recharging a battery of the wearable biological marker sensor while the wearable biological marker sensor is placed within the system.

* * * * *